United States Patent
Tokimoto (10) Patent No.: US 11,559,414 B2
(45) Date of Patent: Jan. 24, 2023

(54) STENT

(71) Applicant: OLYMPUS CORPORATION, Tokyo (JP)

(72) Inventor: Takahira Tokimoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/198,411

(22) Filed: Mar. 11, 2021

(65) Prior Publication Data

US 2021/0220155 A1 Jul. 22, 2021

Related U.S. Application Data (63) Continuation of application No. PCT/JP2018/034005, filed on Sep. 13, 2018.

(51) Int. Cl.
| | |
|---|---|
| A61F 2/90 | (2013.01) |
| A61F 2/86 | (2013.01) |
| A61F 2/89 | (2013.01) |
| A61F 2/04 | (2013.01) |

(52) U.S. Cl.
CPC ............... *A61F 2/90* (2013.01); *A61F 2/86* (2013.01); *A61F 2/89* (2013.01); *A61F 2002/041* (2013.01); *A61F 2002/044* (2013.01); *A61F 2002/045* (2013.01)

(58) Field of Classification Search
CPC ...... A61F 2/90; A61F 2/86; A61F 2/88; A61F 2/89
See application file for complete search history.

(56) References Cited

U.S. PATENT DOCUMENTS

| | | | |
|---|---|---|---|
| 6,241,757 B1 | 6/2001 | An et al. | |
| 6,340,367 B1 | 1/2002 | Stinson et al. | |
| 2013/0289690 A1* | 10/2013 | Thapliyal | A61F 2/88 53/425 |
| 2017/0020542 A1* | 1/2017 | Martin | A61B 17/221 |

FOREIGN PATENT DOCUMENTS

| | | |
|---|---|---|
| JP | H10-272190 A | 10/1998 |
| JP | 2000-060975 A | 2/2000 |
| JP | 2003-079743 A | 3/2003 |
| JP | 2004-528862 A | 9/2004 |
| JP | 3708923 B2 | 10/2005 |
| JP | 2014-522268 A | 9/2014 |
| WO | WO 02/39888 A2 | 5/2002 |
| WO | WO 2012/162437 A1 | 11/2012 |

OTHER PUBLICATIONS

International Search Report dated Dec. 4, 2018 issued in PCT/JP2018/034005.

* cited by examiner

Primary Examiner — Dinah Baria
(74) Attorney, Agent, or Firm — Scully, Scott, Murphy & Presser, P.C.

(57) ABSTRACT

A stent which has a cylindrical tubular shape in which wires cross each other and are woven includes first regions each including a horizontal folding crossing portion in which the wires are folded in an axial direction and cross each other and a vertical folding crossing portion in which the wires are folded in a circumferential direction and cross each other. The first region is a region in which the horizontal folding crossing portion and the vertical folding crossing portion are arranged in the circumferential direction, and the first regions are arranged at intervals in the axial direction.

15 Claims, 7 Drawing Sheets

STENT

The present invention relates to a stent. Priority is claimed on PCT/JP2018/034005, filed Sep. 13, 2018, the content of which is incorporated herein by reference.

In recent years, stent placement has been used to expand and hold a lumen of a tubular organ by placing a stent made of a wire rod (wire) or the like in the diseased part in which stenosis or obstruction occurs in the lumen of the tubular organ in the living body.

BACKGROUND

The stent (self-expandable stent) having self-expandability is delivered by a delivery system to the diseased part in which stenosis or obstruction has occurred in a reduced diameter state. The stent released from the delivery system expands the diameter by self-expandability to expand the stenosis and obstruction.

In many cases, the lumen in which such a stent is placed is bent, and thus the stent needs to have a function of maintaining the shape corresponding to the shape of the bent lumen (pipeline shape-maintaining function). In a case where the stent having the pipeline shape-maintaining function is placed in the bent lumen, the stent can maintain the shape corresponding to the shape of the bent lumen without returning to the original shape of the stent due to reaction force.

The expansion mechanism using the shape memory alloy disclosed in Japanese Patent No. 3708923 can expand the stenosis part of the body. The expansion mechanism disclosed in Japanese Patent No. 3708923 has a "meshing portion" that is extendible and contractible in the axial direction, and can maintain the shape corresponding to the shape of the lumen regardless of the lumen shape of the stenosis part.

SUMMARY

A first aspect of the present invention relates to a stent which has a cylindrical tubular shape in which wires cross each other and are woven, the stent including first regions each including a horizontal folding crossing portion in which the wires are folded in an axial direction and cross each other and a vertical folding crossing portion in which the wires are folded in a circumferential direction and cross each other, in which the first region is a region in which the horizontal folding crossing portion and the vertical folding crossing portion are arranged in the circumferential direction, and the first regions are arranged at intervals in the axial direction.

A second aspect of the present invention relates to a stent which has a cylindrical tubular shape in which wires cross each other and are woven, the stent including a first region which includes a horizontal folding crossing portion in which the wires are folded in an axial direction and cross each other and a vertical folding crossing portion in which the wires are folded in a circumferential direction and cross each other, and is a region in which the horizontal folding crossing portion and the vertical folding crossing portion are arranged in the circumferential direction, and a second region which includes a straight crossing portion in which the wires cross each other in a straight line.

A third aspect of the present invention relates to a stent which has a cylindrical tubular shape in which wires cross each other and are woven, the stent including first regions each including a horizontal folding portion in which the wires are folded in an axial direction to be convex in the axial direction and a vertical folding portion in which the wires are folded in a circumferential direction to be convex in the circumferential direction, in which the first region is a region in which the horizontal folding portion and the vertical folding portion are arranged in the circumferential direction, and the first regions are arranged at intervals in the axial direction.

DETAILED DESCRIPTION OF THE PREFERRED EMBODIMENTS

First Embodiment

A first embodiment of the present invention will be described with reference to FIGS. 1 to 4.

Figure 1:
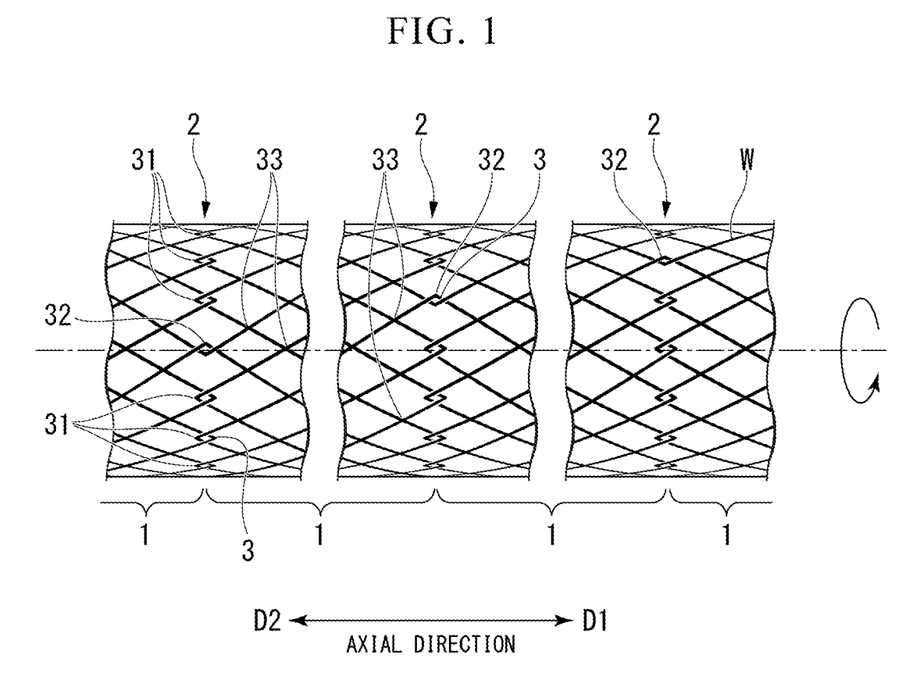
FIG. 1 is a diagram showing an overall configuration of a stent according to a first embodiment.

FIG. 1 is a diagram showing an overall configuration of a stent 100 according to the present embodiment. FIG. 1 shows an overall configuration of the stent 100 in a state of being self-expanded.

The stent 100 is formed by weaving wires W and has a cylindrical tubular shape. The stent 100 has a self-expandability. The stent 100 is placed in the lumen of the alimentary system in living body, such as the bile duct, esophagus, duodenum, small intestine, and large intestine. The stent 100 is mainly used for the purpose of expanding and holding the lumen. The stent 100 according to the present embodiment is not a so-called covered stent in which an outer circumferential surface side thereof is coated with a resin film or the like, but an uncovered stent that is not coated with a film or the like. However, the stent 100 is also capable of being used as a covered stent by being coated with a resin film or the like.

The stent 100 includes, as shown in FIG. 1, a tubular portion 1 and a connecting portion 2. The tubular portion 1 and the connecting portion 2 are alternately arranged in a longitudinal axis direction (hereinafter, referred to as "axial direction"). In the following description, one side of the axial direction of the stent 100 is referred to as a "first axial direction D1", and the other side of the axial direction of the stent 100 is referred to as a "second axial direction D2". Also, one side of the circumferential direction of the stent 100 is referred to as a "first circumferential direction R1", and the other side of the circumferential direction of the stent 100 is referred to as a "second circumferential direction R2".

The wire W configures a crossing portion 3 in which different places of the wires W cross each other. The crossing portion 3 includes a straight crossing portion 33 in which different places of the wires cross each other in a straight line, a horizontal folding crossing portion 31, and a vertical folding crossing portion 32.

The tubular portion 1 is formed in a cylindrical tubular shape in which a mesh is formed on the circumferential surface by weaving the wires W. The tubular portion 1 includes the vertical folding crossing portion 32 and the straight crossing portion 33.

The connecting portion 2 includes the horizontal folding crossing portion 31 and the vertical folding crossing portion 32. The horizontal folding crossing portion 31 and the vertical folding crossing portion 32 are arranged in the circumferential direction. In the present embodiment, one connecting portion 2 includes seven horizontal folding crossing portions 31 and one vertical folding crossing portion 32.

In the horizontal folding crossing portion 31, different places of the wires W (hereinafter, referred to as a "first horizontal folding portion 31a" and a "second horizontal folding portion 31b") are folded in the axial direction and cross each other and the horizontal folding crossing portion 31 is extendible and contractible in the axial direction.

The first horizontal folding portion 31a is a convex portion in which the wire W obliquely extending in the circumferential direction is folded and bent in the axial direction to be convex toward the first axial direction D1.

The second horizontal folding portion 31b is a convex portion in which the wire W obliquely extending in the circumferential direction is folded and bent in the axial direction to be convex toward the second axial direction D2.

The first horizontal folding portion 31a and the second horizontal folding portion 31b cross each other in the radial direction in a "hook shape". The first horizontal folding portion 31a and the second horizontal folding portion 31b are inseparably connected and relatively movable.

In the vertical folding crossing portion 32, different places of the wires W (hereinafter, referred to as a "first vertical folding portion 32a" and a "second vertical folding portion 32b") are folded in the circumferential direction and cross each other. The vertical folding crossing portion 32 is extendible and contractible in the circumferential direction.

The first vertical folding portion 32a is a convex portion in which the wire W obliquely extending in the axial direction is folded and bent in the circumferential direction to be convex toward the first circumferential direction R1.

The second vertical folding portion 32b is a convex portion in which the wire W obliquely extending in the axial direction is folded and bent in the circumferential direction to be convex toward the second circumferential direction R2.

The first vertical folding portion 32a and the second vertical folding portion 32b cross each other in the radial direction in a "hook shape" and are inseparably connected so as to be relatively movable.

The straight crossing portion 33 is formed by crossing the wires W obliquely extending in the circumferential direction and the axial direction with each other without being folded. In the straight crossing portion 33 continuous along the wires W, the wire W alternately passes the radial outer side and the radial inner side of the crossing wire W. The straight crossing portion 33 woven in this way has a repulsive force against extension and contraction in the axial direction and the circumferential direction.

Figure 2:
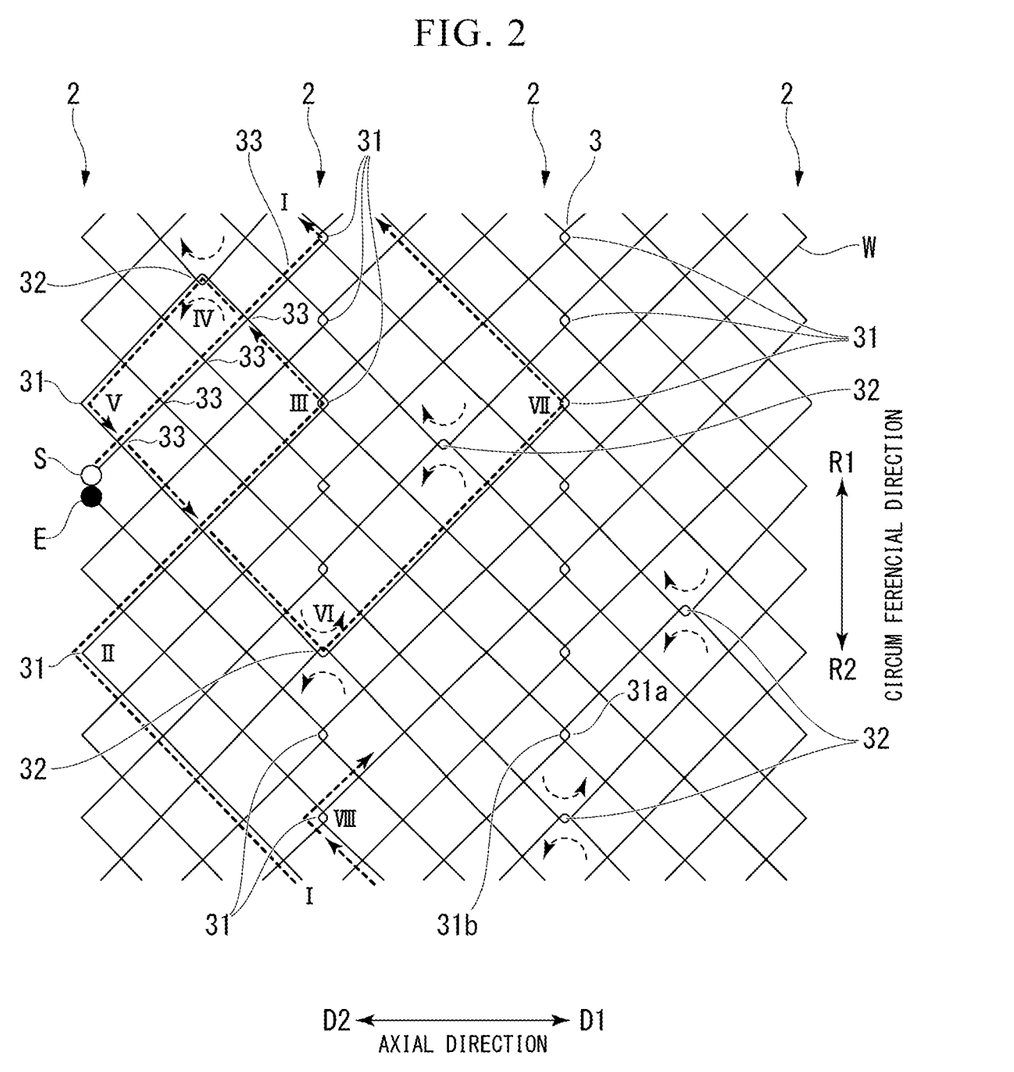
FIG. 2 is a developed view of the stent which is developed in a circumferential direction.

FIG. 2 is a developed view of the stent 100 which is developed in the circumferential direction.

As shown in FIG. 2, the wire W forming the stent 100 extends in a direction oblique (hereinafter, referred to as an "oblique direction") to the circumferential direction and the axial direction from a start position S, and forms the straight crossing portion 33, the horizontal folding crossing portion 31, and the vertical folding crossing portion 32.

The wire W extends in the oblique direction from the start position S and configures one of the crossing wires W in the five continuous straight crossing portions 33. Then, the wire W is folded and configures one of the crossing wires W in the horizontal folding crossing portion 31 of the connecting portion 2 (portion I shown in FIG. 2).

The wire W folded in the axial direction in the connecting portion 2 extends in the oblique direction and configures one of the crossing wires W in the five continuous straight crossing portions 33. Then, the wire W is folded and configures one of the crossing wires W in the horizontal folding crossing portion 31 of the connecting portion 2 (portion II shown in FIG. 2).

The wire W folded in the axial direction in the connecting portion 2 extends in the oblique direction and configures one of the crossing wires W in the five continuous straight crossing portions 33. Then, the wire W is folded and configures one of the crossing wires W in the horizontal folding crossing portion 31 of the connecting portion 2 (portion III shown in FIG. 2).

The wire W folded in the axial direction in the connecting portion 2 extends in the oblique direction and configures one of the crossing wires W in the two continuous straight crossing portions 33. Then, the wire W is folded and configures one of the crossing wires W in the vertical folding crossing portion 32 (portion IV shown in FIG. 2).

The wire W folded in the circumferential direction in the vertical folding crossing portion 32 extends in the oblique direction and configures one of the crossing wires W in the two continuous straight crossing portions 33. Then, the wire W is folded and configures one of the crossing wires W in the horizontal folding crossing portion 31 of the connecting portion 2 (portion V shown in FIG. 2).

The wire W folded in the axial direction in the connecting portion 2 extends in the oblique direction and configures one of the crossing wires W in the five continuous straight crossing portions 33. Then, the wire W is folded and configures one of the crossing wires W in the vertical folding crossing portion 32 of the connecting portion 2 (portion VI shown in FIG. 2).

Due to the wire W configuring one of the crossing wires W in the vertical folding crossing portion 32 of the connecting portion 2, the wire W is woven to continuously form the tubular portions 1 adjacent to each other with the connecting portion 2 therebetween without being cut.

The wire W folded in the circumferential direction in the vertical folding crossing portion 32 of the connecting portion 2 extends in the oblique direction and configures one of the crossing wires W in the five continuous straight crossing portions 33. Then, the wire W is folded and configures one of the crossing wires W in the horizontal folding crossing portion 31 of the connecting portion 2 (portion VII shown in FIG. 2).

The wire W folded in the axial direction in the connecting portion 2 extends in the oblique direction and configures one of the crossing wires W in the five continuous straight crossing portions 33. Then, the wire W is folded and configures one of the crossing wires W in the horizontal folding crossing portion 31 of the connecting portion 2 (portion VIII shown in FIG. 2).

The wire W forms the other horizontal folding crossing portion 31, the other vertical folding crossing portion 32, and the other straight crossing portion 33 by the same method, and is woven to an end point E without being cut.

Both end portions of the wire W positioned at the start position S and the end point E are connected by using a joining method, such as swaging, laser welding, or brazing. FIG. 2 shows the wire W joins the end portion of the horizontal folding crossing portion 31, but the wire W may join the straight line portion instead of the end portion of the horizontal folding crossing portion 31 in consideration that stress concentration is likely to occur at the end portion.

The wire W is made of a super-elastic alloy containing NiTi as a main material. The super-elastic alloy containing NiTi as the main material is not permanently deformed at the time of weaving, and the woven shape is held by applying heat treatment in the woven state.

Hereinafter, the operation of the stent 100 will be described.

The stent 100 is stored in the delivery system in a reduced diameter state and delivered to the diseased part in which stenosis or obstruction occurs. The stent 100 is released from the delivery system and expands the diameter by self-expandability to expand the stenosis and obstruction. Since the stent 100 has a simple configuration, the storage diameter is capable of being reduced in a case where the stent 100 is stored in the delivery system.

Figure 3:
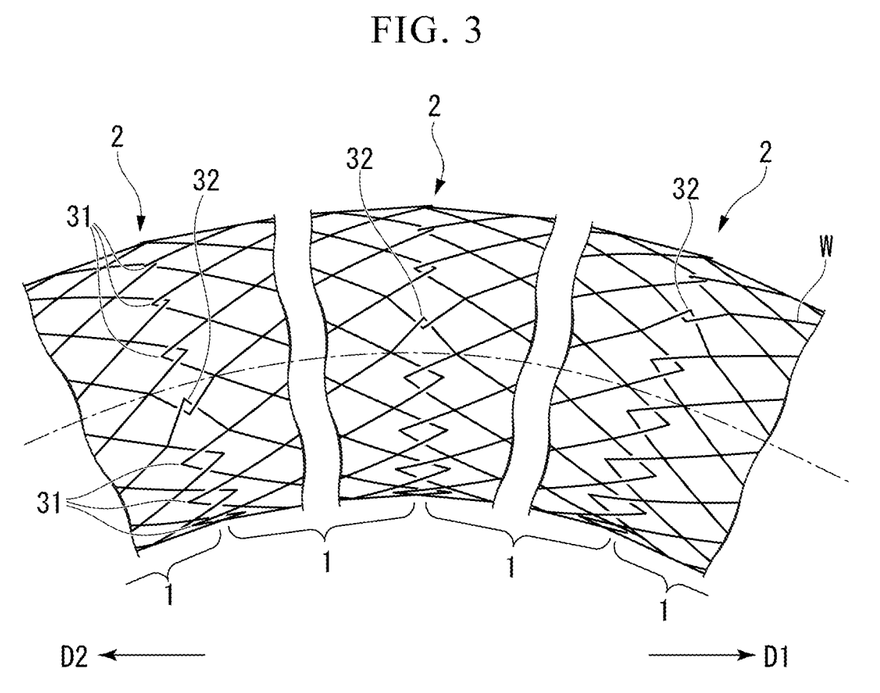
FIG. 3 shows the bending stent.

FIG. 3 shows the bending stent 100. The connecting portion 2 is configured by the horizontal folding crossing portion 31 that is extendible and contractible in the axial direction and the vertical folding crossing portion 32 that is extendible and contractible in the circumferential direction. In the connecting portion 2, since the number of the horizontal folding crossing portions 31 extendible and contractible in the axial direction is larger than the number of the vertical folding crossing portions 32 extendible and contractible in the circumferential direction, the adjacent tubular portions 1 are capable of being suitably moved relative to each other in the axial direction. Hereinafter, a deformation of the connecting portion 2 due to the relative movement of the adjacent tubular portions 1 is referred to as "slip-deformation".

In the stent 100, in a case where the entire stent 100 is bent with respect to the longitudinal axis as shown in FIG. 3, the horizontal folding crossing portions 31 arranged in the circumferential direction are "slip-deformed" and bent in the axial direction without "elastic deformation" of the wire W that is made of super-elastic alloy. As a result, the stent 100 does not return to the original shape, and maintains the bent shape. That is, the stent 100 has a function of maintaining the shape corresponding to the shape of the bent lumen (pipeline shape-maintaining function).

Here, the vertical folding crossing portion 32 of the connecting portion 2 is extendible and contractible in the circumferential direction and not extendible and contractible in the axial direction. Therefore, the vertical folding crossing portion 32 does not contribute to improvement of the pipeline shape-maintaining function of the connecting portion 2 in a case where the stent 100 is bent. As shown in FIG. 3, the vertical folding crossing portion 32 of the connecting portion 2 does not extend and contract in the axial direction, and a reaction force that returns to the original shape of the stent 100 is generated. Therefore, it is considered that forming the vertical folding crossing portion 32 in the connecting portion 2 is disadvantageous from the viewpoint of the pipeline shape-maintaining function. However, by forming one or more vertical folding crossing portions 32 in the connecting portion 2, the stent 100 is capable of being woven without cutting the wire W.

Figure 4:
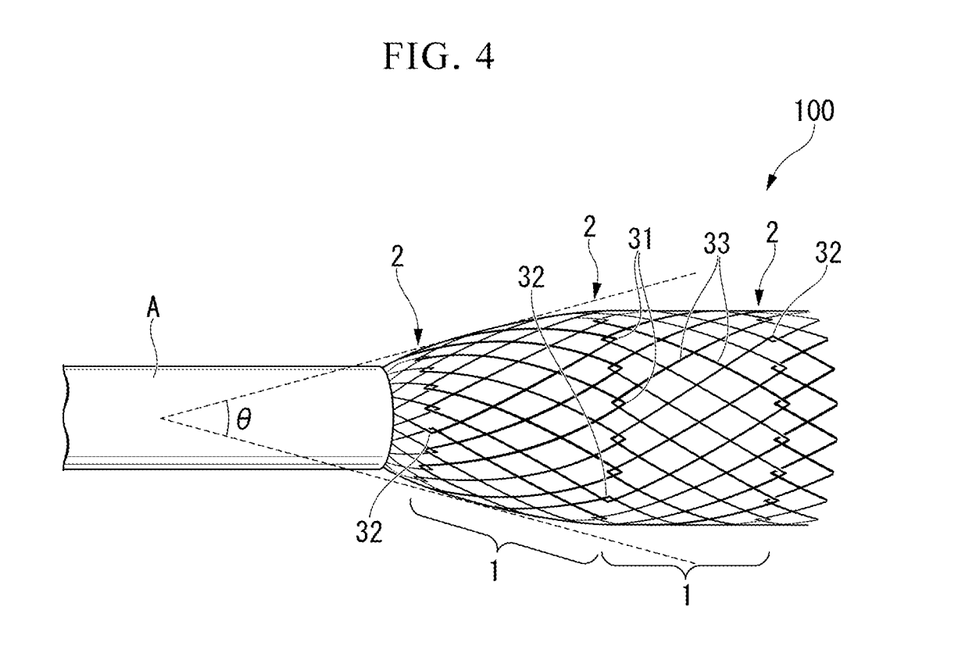
FIG. 4 shows the stent in a case of being released from a delivery system.

FIG. 4 shows the stent 100 in a case of being released from the delivery system.

In a case where the stent 100 is released from an outer sheath A at a distal end of the delivery system, since a spread angle θ of the stent 100 is capable of being reduced, so that the stent 100 is capable of being easily restored (recaptured) in the delivery system. That is, the stent 100 has a recapture function capable of being easily restored (recaptured) in the delivery system.

In the expansion mechanism disclosed in Japanese Patent No. 3708923, the number of the "meshing portions" crossing in the hook shape, and the spread angle of the expansion mechanism are significantly large in a case where the expansion mechanism is released. Therefore, it is necessary to apply a large force in a case where the expansion mechanism is restored (recaptured) in the delivery system, and restoring (recapturing) is difficult.

The stent 100 of the present embodiment has the connecting portions 2 crossing in the hook shape. The connecting portion 2 including a large number of horizontal folding crossing portions 31 slip-deformed in the axial direction is likely to spread in the radial direction in a case of releasing, as compared with the tubular portion 1 configured with the straight crossing portion 33 that uniformly spreads in the longitudinal axis direction. However, in the stent 100, the connecting portion 2 that is capable of being slip-deformed and the tubular portion 1 that is not capable of being slip-deformed are disposed in the axial direction. Therefore, in a case where the stent 100 is released, the spread angle θ of the stent 100 is capable of being reduced as compared with the expansion mechanism disclosed in Japanese Patent No. 3708923.

With the stent 100 according to the present embodiment, the stent 100 has both the pipeline shape-maintaining function and the recapture function capable of being easily restored in the delivery system.

Since the stent 100 according to the present embodiment includes the horizontal folding crossing portion 31 that is extendible and contractible and the vertical folding crossing portion 32 that is extendible and contractible, and these two types of extendible and contractible crossing portions are disposed, the stent 100 is capable of being formed without cutting the wire W, and the degree of freedom in design is high.

In the stent 100 according to the present embodiment, the degree of freedom in design is high, so that the stent 100 having the pipeline shape-maintaining function and the recapture function is capable of being formed. By forming one or more vertical folding crossing portions 32 in the connecting portion 2, the pipeline shape-maintaining function of the connecting portion 2 decreases, but it is advantageous in that the stent 100 is capable of being woven without cutting the wire W. Since the stent 100 has few wire joints, the durability of the stent 100 is improved as compared with a stent having many wire joints.

As described above, the first embodiment of the present invention has been described in detail with reference to the drawings. However, the specific configuration is not limited to this embodiment, and includes design changes and the like without departing from the scope of the present invention. Further, the constituent elements shown in the first embodiment described above and modification examples described below are capable of being appropriately combined and configured.

Modification Example 1

For example, in the above embodiment, the connecting portion 2 that is capable of being slip-deformed and the straight crossing portion 33 that is not slip-deformed are disposed in the axial direction in the stent 100, and therefore the stent 100 has both the pipeline shape-maintaining function and the recapture function. However, the aspect of the stent is not limited thereto. In a case of further improving the recapture function, the number of the straight crossing portions 33 woven in the axial direction of the tubular portion may be increased. However, since the pipeline shape-maintaining function is suppressed as a ratio of the straight crossing portion 33 in the stent increases, it is desirable that the ratio of the straight crossing portion 33 in the stent be decided in consideration of the balance between the recapture function and the pipeline shape-maintaining function.

Modification Example 2

For example, in the above embodiment, in the vertical folding crossing portion 32, the first vertical folding portion 32a and the second vertical folding portion 32b cross each other in the "hook shape" in the radial direction. However, the aspect of the vertical folding crossing portion is not limited thereto. FIGS. 5 to 8 are diagrams showing modification examples of the vertical folding crossing portion of the stent. The vertical folding crossing portions of the modification examples are suppressed from being slip-deformed in the circumferential direction. Therefore, in a case where it is desired to suppress the slip-deformation in the circumferential direction, such as a case where it is necessary to place the stent in the lumen having a strong stenosis force, the vertical folding crossing portion of the modification example may be used as an alternative to the vertical folding crossing portion 32 according to the above embodiment.

Figure 5:
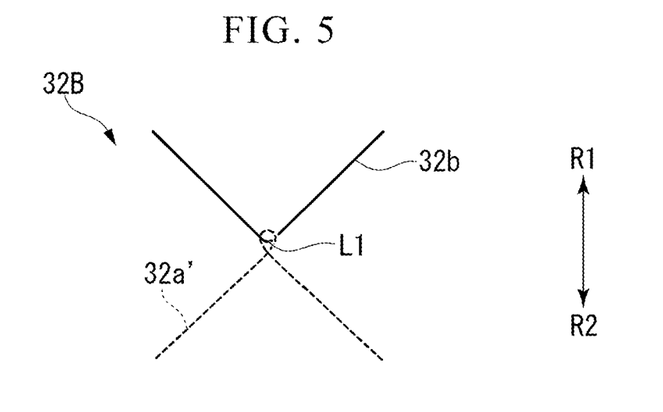
FIG. 5 is a diagram showing a modification example of a vertical folding crossing portion of the stent.

In a vertical folding crossing portion 32B of the modification example shown in FIG. 5, a first vertical folding portion 32a' and the second vertical folding portion 32b cross each other. The first vertical folding portion 32a' is a convex portion in which the wire W obliquely extends in the axial direction, loops, is folded and bent to form a twisted portion (first twisted portion) L1. The first vertical folding portion 32a' is convex toward the first circumferential direction R1. The second vertical folding portion 32b passes through the first twisted portion L1 of the first vertical folding portion 32a', and the vertical folding crossing portion 32B is suppressed from being slip-deformed in the circumferential direction.

Figure 6:
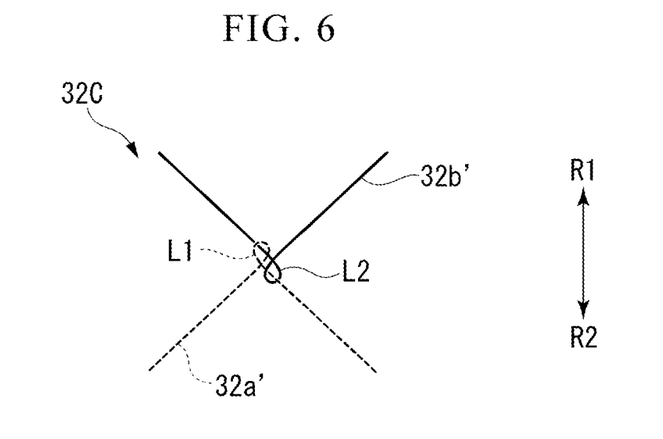
FIG. 6 is a diagram showing a modification example of a vertical folding crossing portion of the stent.

In a vertical folding crossing portion 32C of the modification example shown in FIG. 6, the first vertical folding portion 32a' and the second vertical folding portion 32b' cross each other. The second vertical folding portion 32b' is a convex portion in which the wire W obliquely extends in the axial direction, loops, is folded, and bent to form a twisted portion (second twisted portion) L2. The second vertical folding portion 32b' is convex toward the second circumferential direction R2. The first vertical folding portion 32a' passes through the second twisted portion L2 of the second vertical folding portion 32b' and the second vertical folding portion 32b' passes through the first twisted portion L1 of the first vertical folding portion 32a', so that the vertical folding crossing portion 32C is suppressed from being slip-deformed in the circumferential direction.

Figure 7:
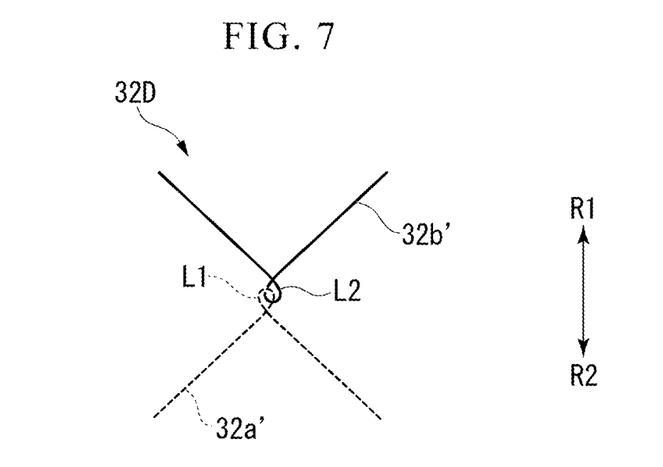
FIG. 7 is a diagram showing a modification example of a vertical folding crossing portion of the stent.

In a vertical folding crossing portion 32D of the modification example shown in FIG. 7, a first vertical folding portion 32a' and the second vertical folding portion 32b' cross each other. The first twisted portion L1 of the first vertical folding portion 32a' and the second twisted portion L2 of the second vertical folding portion 32b' cross each other. Therefore, the vertical folding crossing portion 32D does not the slip-deformed in the circumferential direction, and conversely has a repulsive force against extension and contraction in the circumferential direction.

Figure 8:
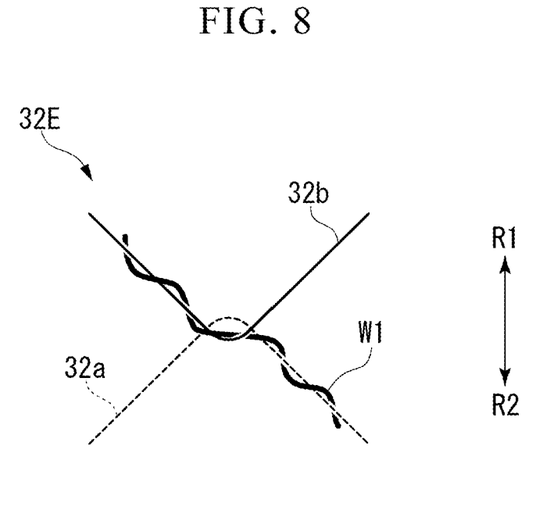
FIG. 8 is a diagram showing a modification example of a vertical folding crossing portion of the stent.

In a vertical folding crossing portion 32E of the modification example shown in FIG. 8, another wire W1 is spirally wound around the first vertical folding portion 32a and the second vertical folding portion 32b crossing in the "hook shape" in the radial direction. Therefore, the vertical folding crossing portion 32E does not the slip-deformed in the circumferential direction, and conversely has a repulsive force against extension and contraction in the circumferential direction.

Second Embodiment

A second embodiment of the present invention will be described with reference to FIG. 9. In the following description, the same components as those already described will be designated by the same reference numerals and the description thereof will be omitted. A stent 100B according to the second embodiment is different from the stent 100 according to the first embodiment in that the tubular portion and the connecting portion are not distinguished.

The stent 100B is formed by weaving wires W and has a cylindrical tubular shape.

The wire W configures a crossing portion 3 in which different places of the wires W cross each other. The crossing portion 3 includes the horizontal folding crossing portion 31 and the vertical folding crossing portion 32.

Figure 9:
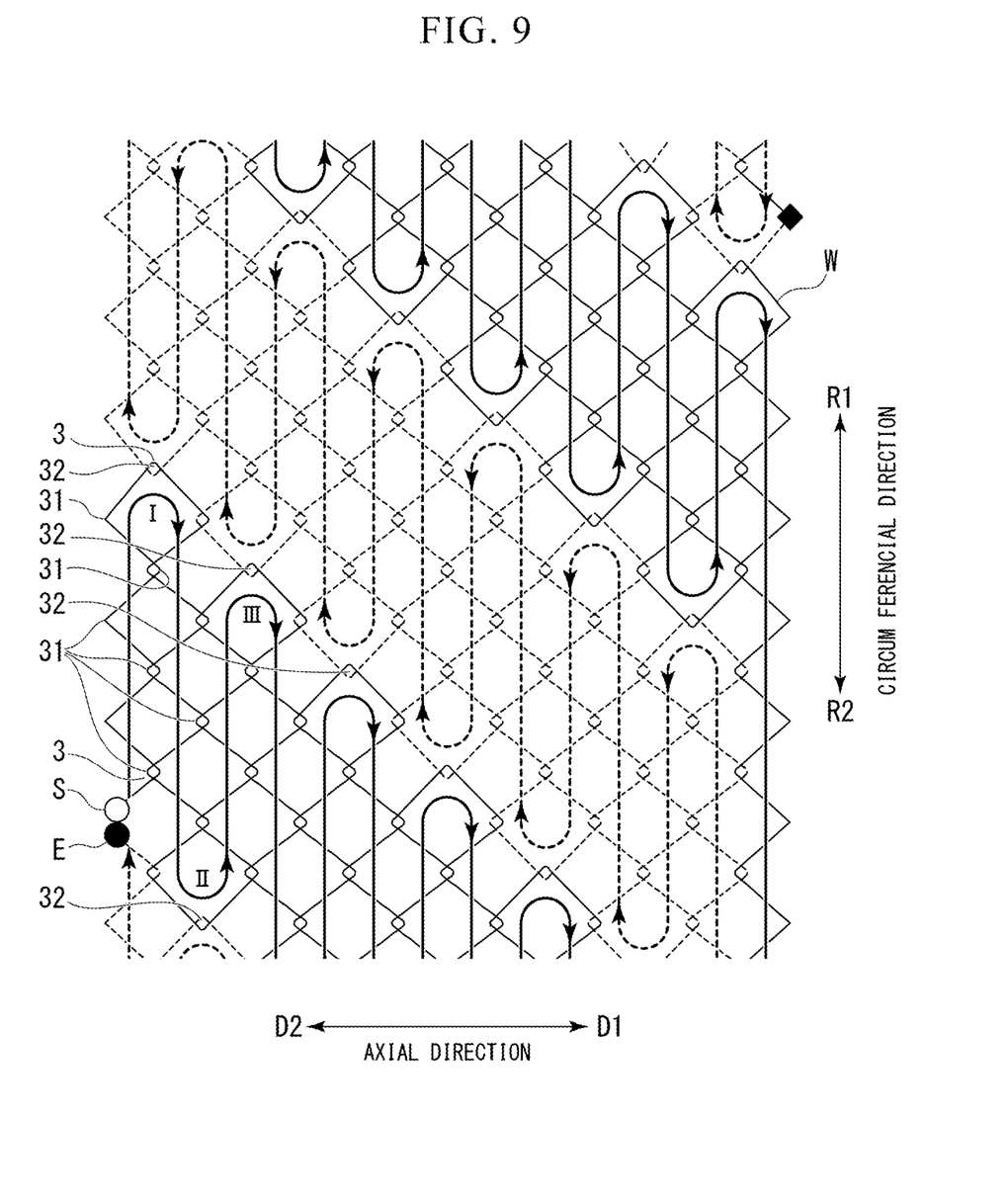
FIG. 9 is a developed view of a stent according to a second embodiment which is developed in a circumferential direction.

FIG. 9 is a developed view of the stent 100B which is developed in the circumferential direction.

As shown in FIG. 9, the wire W forming the stent 100B extends in a direction oblique (hereinafter, referred to as an "oblique direction") to the circumferential direction and the axial direction from a start position S, and forms the horizontal folding crossing portion 31 and the vertical folding crossing portion 32.

The wire W extends in the oblique direction from the start position S, repeats bending, and configures one of the crossing wires W in six continuous horizontal folding crossing portions 31. Then, the wire W configures one of the crossing wires W in the vertical folding crossing portion 32 (portion I shown in FIG. 9).

The wire W folded in the circumferential direction in the vertical folding crossing portion 32 extends in the oblique direction, repeats bending, and configures one of the crossing wires W in the six continuous horizontal folding crossing portions 31. Then, the wire W configures one of the crossing wires W in the vertical folding crossing portion 32 (portion II shown in FIG. 9).

The wire W folded in the circumferential direction in the vertical folding crossing portion 32 extends in the oblique direction, repeats bending, and configures one of the crossing wires W in eight continuous horizontal folding crossing portions 31. Then, the wire W is folded and configures one of the crossing wires W in the vertical folding crossing portion 32 (portion III shown in FIG. 9).

The vertical folding crossing portion 32 of the portion I shown in FIG. 9 and the vertical folding crossing portion 32 of the portion III shown in FIG. 9 are arranged in the oblique direction.

The wire W forms the horizontal folding crossing portions 31 and the vertical folding crossing portions 32 by the same method, and is woven to an end point E without being cut.

The stent 100B according to the present embodiment includes the horizontal folding crossing portion 31 that is extendible and contractible and the vertical folding crossing portion 32 that is extendible and contractible, and by disposing these two types of extendible and contractible crossing portions, the stent 100B is capable of being formed without cutting the wire W, and the degree of freedom in design is high.

Modification Example 3

Figure 10:
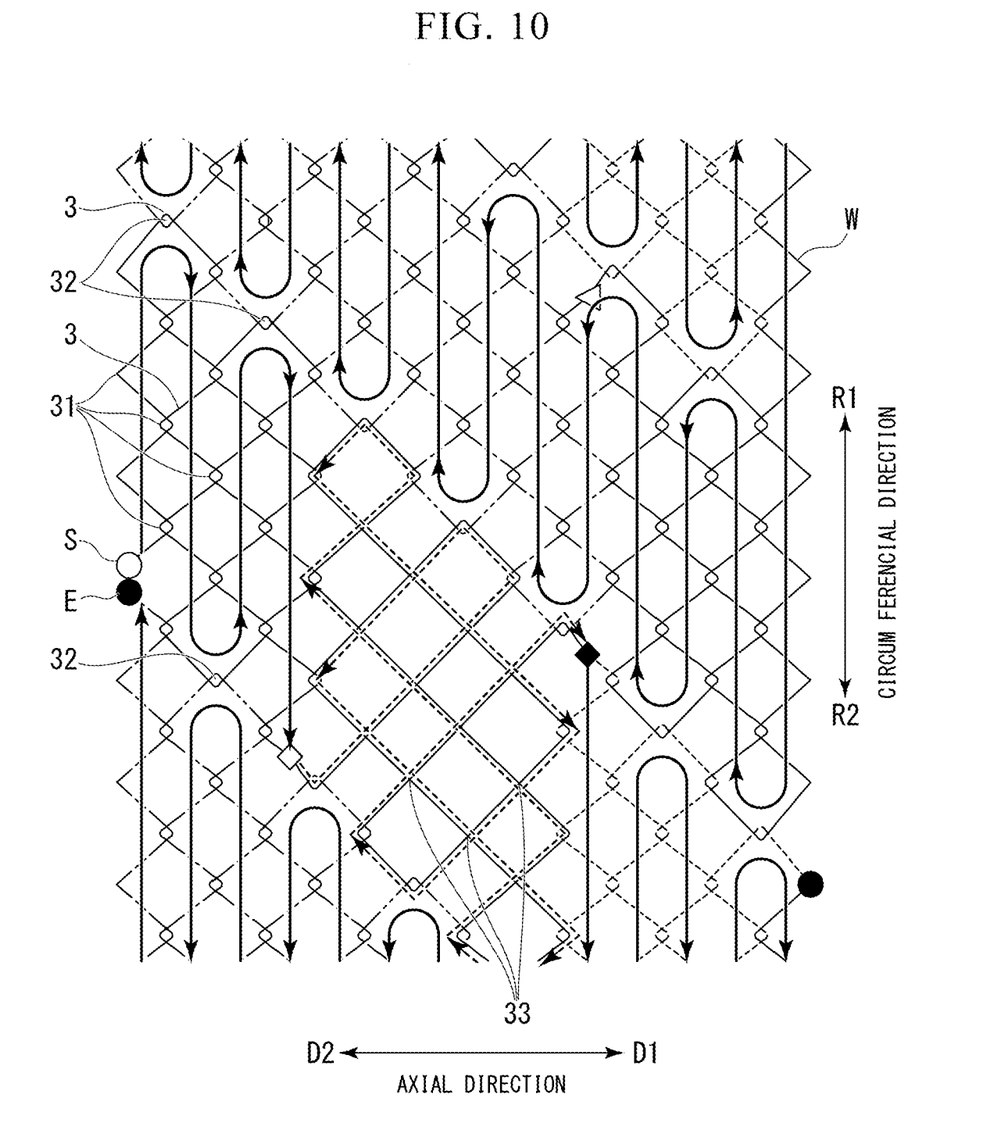
FIG. 10 is a developed view of a modification example of the stent which is developed in a circumferential direction.

In the above embodiment, the stent 100B is formed by the horizontal folding crossing portion 31 and the vertical folding crossing portion 32 without the straight crossing portion 33, but the aspect of the stent is not limited thereto. The stent may have the straight crossing portion 33 in a part of the stent, as in the stent 100C which is the modification example of the stent 100B as shown in FIG. 10. After ensuring the degree of freedom in design by the horizontal folding crossing portion 31 and the vertical folding crossing portion 32, the straight crossing portion 33 having the repulsive force may be appropriately disposed at the place where the repulsive force is required.

As described above, the second embodiment of the present invention has been described in detail with reference to the drawings, but the specific configuration is not limited to this embodiment, and includes design changes and the like without departing from the scope of the present invention. Further, the constituent elements shown in the embodiments described above and the modification examples are capable of being appropriately combined and configured.

What is claimed is:

1. A stent comprising:
   a woven wire body having first and second regions alternating in an axial direction of the woven wire body, the woven wire body having a cylindrical tubular shape, wherein:
   each first region comprising:
      one or more horizontal folding linking portions in which two wires are folded in an axial direction to link with each other, and
      one or more vertical folding linking portions in which two wires are folded in a circumferential direction to link with each other, and
   each second region comprising a plurality of crossing portions in which two wires cross each other without linking,
   in each first region, the one or more horizontal folding linking portions and the one or more vertical folding linking portions are arranged in the circumferential direction,
   in each second region, the plurality of crossing portions are arranged in the circumferential direction, and
   in each first region, a number of the horizontal folding linking portions is larger than a number of the vertical folding linking portions.

2. The stent according to claim 1, wherein the one or more vertical folding linking portions are formed by a first wire of the two wires bent to be convex toward a first circumferential direction side that is one side of the circumferential direction and a second wire of the two wires bent to be convex toward a second circumferential direction side that is the other side of the circumferential direction, which cross each other in a radial direction.

3. The stent according to claim 2, wherein the first wire loops to form a first twisted portion, and the first twisted portion crosses the second wire.

4. The stent according to claim 2, wherein the second wire loops to form a second twisted portion, and the second twisted portion crosses the first wire portion.

5. The stent according to claim 4, wherein the first twisted portion and the second twisted portion cross each other.

6. The stent according to claim 2, wherein the one or more vertical folding linking portions further include a twisting wire spirally wound around the first wire and the second wire, wherein one end of the twisting wire is twisted around a portion of one of the two wires of the one or more vertical folding linking portions and another end of the twisting wire is twisted around a portion of an other of the two wires of the one or more vertical linking portions.

7. The stent according to claim 1, wherein the one or more horizontal folding linking portions are formed by a first wire of the two wires bent to be convex toward a first axial direction side that is one side of the axial direction and a second wire of the two wires bent to be convex toward a second axial direction side that is the other side of the axial direction, which cross each other in a radial direction.

8. The stent according to claim 1, wherein the woven wire body is made of a super-elastic alloy, and the woven wire body has self-expandability for expanding a lumen of a living body.

9. A stent comprising:
   a woven wire body having first regions, the woven wire body having a cylindrical tubular shape, wherein:
   each first region comprising:
      one or more horizontal folding linking portions in which two wires are folded in an axial direction to link with each other, and
      one or more vertical folding linking portions in which first and second wires are folded in a circumferential direction to link with each other, and
   in each first region, the one or more horizontal folding linking portions and the one or more vertical folding linking portions are arranged in the circumferential direction; and
   the vertical folding linking portions further include a twisting wire spirally wound around the first and second wires, wherein one end of the twisting wire is twisted around a portion of one of the first and second wires of the one or more vertical folding linking portions and another end of the twisting wire is twisted around a portion of an other of the first and second wires of the one or more vertical linking portions.

10. The stent according to claim 9, wherein in each first region, a number of the horizontal folding linking portions is larger than the number of the vertical folding linking portions.

11. The stent according to claim 9, wherein:
   the woven wire body further having second regions, the first and second regions alternating in an axial direction of the woven wire body;
   each second region comprising a plurality of crossing portions in which two wires cross each other without linking; and
   in each second region, the plurality of crossing portions are arranged in the circumferential direction.

12. The stent according to claim 9, wherein the woven wire body is made of a super-elastic alloy, and the woven wire body has self-expandability for expanding a lumen of a living body.

13. A stent comprising:
   a woven wire body having first and second regions alternating in an axial direction of the woven wire body, the woven wire body having a cylindrical tubular shape, wherein:
   each first region comprising:
      one or more horizontal folding linking portions in which two wires are folded in an axial direction to be convex in the axial direction, and
      one or more vertical folding linking portions in which two-wires are folded in a circumferential direction to be convex in the circumferential direction,
   wherein each second region comprising a plurality of crossing portions in which two wires cross each other without linking,
   in each first region, the one or more horizontal folding linking portions and the one or more vertical folding linking portions are arranged in the circumferential direction; and
   in each first region, a number of the horizontal folding linking portions is larger than the number of the vertical folding linking portions.

14. The stent according to claim 13, wherein the woven wire body is made of a super-elastic alloy, and the woven wire body has self-expandability for expanding a lumen of a living body.

15. The stent according to claim 13, wherein the vertical folding linking portions further include a twisting wire spirally wound around the first and second wires, wherein one end of the twisting wire is twisted around a portion of one of the two wires of the one or more vertical folding linking portions and another end of the twisting wire is twisted around a portion of an other of the two wires of the one or more vertical linking portions.

* * * * *